United States Patent [19]
Hirose et al.

[11] 3,950,440
[45] Apr. 13, 1976

[54] PROCESS FOR OXIDIZING OLEFINS

[75] Inventors: Isao Hirose, Mitaka; Kazutoshi Funabashi, Hino; Takeshi Fujii, Iwakuni; Kiyoshi Kawajiri, Hiroshima, all of Japan

[73] Assignee: Teijin Ltd., Osaka, Japan

[22] Filed: Mar. 9, 1970

[21] Appl. No.: 17,589

Related U.S. Application Data

[63] Continuation-in-part of Ser. No. 615,423, Feb. 13, 1967, abandoned.

[30] Foreign Application Priority Data

Feb. 17, 1966 Japan.................................. 41-9565
Feb. 17, 1966 Japan.................................. 41-9566

[52] U.S. Cl....... 260/635 H; 260/597 R; 260/604 R; 260/634
[51] Int. Cl.².................. C07C 29/04; C07C 27/12
[58] Field of Search................................. 260/635 H

[56] References Cited
UNITED STATES PATENTS

| | | | |
|---|---|---|---|
| 3,048,636 | 8/1962 | Grinstead........................ | 260/635 H |
| 3,118,001 | 1/1964 | Riemenschneider................ | 260/586 |
| 3,154,586 | 10/1964 | Bander et al. ...................... | 260/597 |
| 3,360,548 | 12/1967 | Clark et al. ...................... | 260/635 H |
| 3,479,395 | 11/1969 | Huguet ........................... | 260/635 H |

FOREIGN PATENTS OR APPLICATIONS

| | | | |
|---|---|---|---|
| 1,518,962 | 2/1968 | France........................... | 260/635 H |
| 1,344,652 | 10/1963 | France............................ | 260/634 |

*Primary Examiner*—Joseph E. Evans
*Attorney, Agent, or Firm*—Sherman & Shalloway

[57] ABSTRACT

A process for the manufacture of an alkylene glycol having 2 – 4 carbon atoms, which comprises oxidizing an unsubstituted aliphatic olefin having 2 – 4 carbon atoms by contact with a water-soluble thallic salt in the presence of water, characterised in that at least one kind of ions selected from ions of chlorine and bromine is present in the reaction system in an amount such that the atomic ratio of the said ion or ions to thallium atom is at least 5, and said oxidation is carried out at a temperature of 120°– 200°C.

4 Claims, 1 Drawing Figure

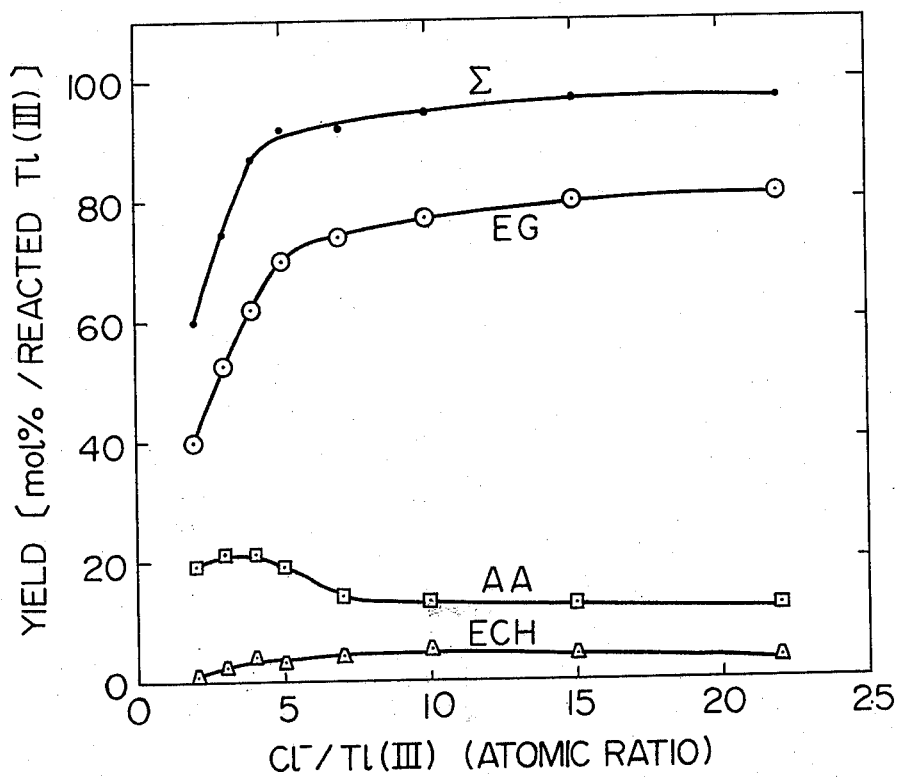

PROCESS FOR OXIDIZING OLEFINS

This application is a continuation-in-part of application Ser. No. 615,423, filed Feb. 13, 1967, now abandoned.

This invention relates to a process for oxidising an unsubstituted aliphatic olefines having 2 to 4 carbon atoms. More particularly, this invention relates to a process for obtaining corresponding glycols by oxidising the said olefines with a water-soluble thallic salt [hereinafter may be referred to as Tl (III)] in the presence of water and halogen ions.

Heretofore, to prepare glycols from olefines, there has been employed a method by which a halohydrin is reacted with an alkali to be converted to an olefine oxide, which is then hydrolysed, or an olefine is directly oxidised with air in a gaseous phase in the presence of a silver catalyst to an olefine oxide, which is then hydrolysed.

These methods, however, are not necessarily satisfactory as commercial methods of manufacturing glycols because they result in low yields of the final products owing to side-reactions or because they necessitate a great quantity of other materials such as halogens, and hydrogen halide or a process consisting of several steps.

According to the process of this invention, however, corresponding glycols can be manufactured easily at high yields by contacting olefines with Tl (III) in the presence of water and halogen ions (in neutrality or acidity) at a temperature of 120° to 200°C.

In this invention, when in the concurrent presence of a metal salt (hereinafter to be referred to as Redox metal salt) capable of possessing different valences under reaction conditions and oxidisable with molecular oxygen, together with water, a thallium salt and halogen ions (in neutrality or acidity), molecular oxygen is contacted with these and a thallous salt (to be referred to as Tl (I) hereinafter) concurrently or subsequently formed is repeatedly oxidised to Tl (III).

A method of oxidising olefines by using a thallic salt is reported in U.S. Pat. No. 3,048,636. The method of this patent is a method of obtaining at least one compound selected from the group consisting of glycols, aldehydes and ketones by oxidising an olefine with the use of an equimolar amount, based on an olefinic hydrocarbon, of an acid aqueous solution of a thallic salt, and as the thallic salt, the use of thallic nitrate and thallic sulphate is recommended.

However, this U.S. Pat. is interesting only as a chemical literature, and it was totally impossible to produce glycols commercially by using the method disclosed in this Patent because the yield of glycol from olefin was low, the glycol was always formed together with a considerable amount of such by-products as acetaldehyde and glycol aldehyde and also because a method of converting a thallous salt formed after the reaction easily into a thallic salt was not known.

We have extensively studied the action of a thallic salt on olefines, and found that when bromine ions and/or chlorine ions are present in the reaction system, another reaction, in addition to the reaction disclosed in the said U.S. Patent, takes place to form alkylene halohydrin, that by utilising this another reaction, alkylene glycol can be prepared at a very high yield, and that such a method can be applied to a commercial production. The present invention pertains to the same field as the said U.S. Patent so far as olefines are oxidised with a thallic salt.

The reaction mechanism of the method of the said U.S. Patent is reported in Journal of Organic Chemistry, Vol. 26, pages 238–240 by Robert R. Grinstead, the inventor for the said U.S. Patent. According to this report, glycol, aldehyde and ketone are formed by the following reactions:

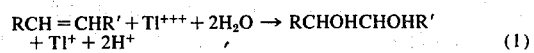

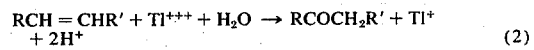

We have studied the case where $Br^-$ and/or $Cl^-$ are present in the said reaction system, and found that the following reactions take place, for example, when ethylene is used.

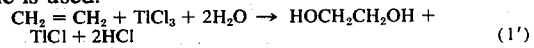

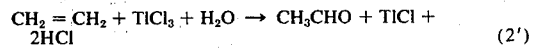

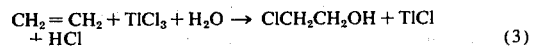

As already mentioned, that the reactions (1') and (2') take place by the reaction of an olefine with a thallic salt is disclosed in the said U.S. Patent, but the reaction (3) above is not at all taught by the said U.S. Patent. However, we have found that the said reaction (3) also takes place between an olefine and a thallic salt when $Cl^-$ and/or $Br^-$ are present, and that when the reaction conditions are appropriately adjusted, it is possible to produce alkylene halohydrin mainly takes place. Thus, according to this invention, it has been found that by adjusting the reaction conditions positively to form an alkylene halohydrin is formed, it is possible to obtain the corresponding glycol at a high yeild by utilising the said reaction (3).

According to this invention, it is possible to direct the reaction so as to mainly induce a reaction to produce an alkylene halohydrin according to the said formula (3), by oxidising at least one unsubstituted aliphatic olefine having 2–4 carbon atoms selected from the group consisting of ethylene, propylene, butene-1, butene-2 and isobutene by contact with chlorine ions and/or bromine ions at an atomic ratio of a total of these ions to the thallium atom adjusted to at least 5, and the reaction (3) is induced under the conditions such that the formed alkylene halohydrin undergoes hydrolysis, the said alkylene halohydrin can be converted to an alkylene glycol in the same reaction system almost simultaneously or subsequently. Incidentally, the alkylene halohydrin referred to herein is an alkylene chlorohydrin and/or alkylene bromohydrin having the number of carbon atoms corresponding to the said olefine with 2–4 carbon atoms, and the alkylene glycol is also a glycol having carbon atoms corresponding to the number of carbon atoms of the said olefine. This is the same throughout the specification.

It has been found according to the researches of the inventors that the atomic ratio of chlorine ions and/or bromine ions to the thallium atom plays an important role in the selectivity of reaction when an unsubstituted aliphatic olefine with 2–4 carbon atoms (hereinafter may be referred to simply as olefine) is reacted with an aqueous solution of a water-soluble thallic salt.

This will be explained with reference to the accompanying graph, which shows the results of the oxidation of ethylene according to the conditions of Controls 1–3 and Examples 1–5 and in which the abscissa represents an atomic ratio of chlorine ions (Cl⁻) to a thallic atom [Tl(III)] and the ordinate shows a yield of the product based on the reacted thallic salt. The curves ECH, EG and AA respectively show the yeild of ethylene chlorohydrin, ethylene glycol and acetaldehyde.

As is clear from this graph, when the atomic ratio of Cl⁻/Tl(III) is 4 or less, the yield of ethylene glycol is low. However, when the atomic ratio of Cl⁻/Tl(III) is above 5, especially above 6, the formation of ethylene glycol is markedly increased.

Since ethylene chlorohydrin is easily hydrolysed to ethylene glycol, it is clear that ethylene glycol is obtained easily.

Accordingly, it is necessary in this invention to adjust the atomic ratio of Cl⁻ and/or Br⁻ to Tl(III) in the reaction medium to at least 5, preferably at least 6. There is no particular restriction on the upper limit of the Cl⁻ (and/or Br⁻)/Tl(III) ratio. But the reaction rate tends to get smaller as the concentration of these halogen ions become greater. Practically, the said atomic ratio may be 5–100 or greater.

As the halogen to be used, any compound may be used if only it is in the ionic form under the reaction conditions, and usually it is used in the form of hydrogen halide, thallium halide and/or redox metal halide such as chlorides and bromides of copper and iron. In order to prevent the reaction system from getting excessively acidic, the chloride or bromide of an alkali metal such as sodium, potassium and lithium and an alkaline earth metal such as calcium and magnesium or other metals which do not directly participate in the reaction may also be used.

According to this invention, the chlorine ions and bromine ions may be present concurrently in the reaction medium. As alkylene bromohydrin is hydrolysable at a lower temperature than in the case of alkylene chlorohydrin, the presence in the reaction system of Br⁻ sometimes brings about favorable results.

It is however better to avoid the copresence of too great a quantity of fluorine and iodine ions because fluorine tends to cause the formation of carbonyl compounds as by-products and iodine tends to reduce Tl(III). The concentration of chlorine ions and/or bromine ions may advantageously be 0.1 to 10 moles/liter based on the reaction medium, but not necessarily be confined to this range.

The Tl(III) used in the reaction may be any kind of salt if only it is soluble in the reaction medium even in a small amount. But the essential feature of this invention is that the reaction should always be carried out in the presence of chlorine ions and/or bromine ions. As the reaction itself is prone to undergo the influence of these ions, it is convenient if the thallic salt to be used is in the form of chloride or bromide.

Practically, Tl(III) is used in the concentration of 0.1 to 50% by weight based on the medium, but may be of a lower or higher concentration.

If TlCl₃ or TlBr₃ is used as the thallic salt, it is necessary to add a chlorine and/or bromine ion (other than a thallic salt) donor as mentioned above to the reaction system in addition to a thallic chloride or thallic bromide since the atomic ratio of Cl⁻ and/or Br⁻ to Tl should be, as mentioned above, adjusted to at least 5.

Water is the most convenient medium to be used in the reaction, and the reaction is ordinarily carried out in an aqueous solution. Besides water, organic compounds miscible with water can be used as the medium.

Especially, glycol formed by the reaction is suitable as the reaction medium, and the reaction proceeds in the presence of glycol without any difficulty. Likewise, halohydrin formed by the reaction can also be used as the reaction medium together with water.

The use of monohydric alcohols such as methyl alcohol, ethyl alcohol and acetone and carbonyl compounds is not desirable as they tend to reduce Tl(III).

In the reaction of this invention, water is also a reactant. Therefore, the presence of water or water vapour is indispensable when any kind of liquid is used as the reaction medium.

The pH of the reaction medium may be neutral or acidic, but it is preferable that the pH should be adjusted to less than 4.

The olefines may be used directly or on dilution with a suitable diluent such as oxygen, air, nitrogen, ethane and propane.

Generally, olefines having more carbon atoms tend more to form carbonyl compounds. Ethylene is the most suitable, and propylene and butene come mext. Among the olefines having 4 carbon atoms, 1-olefines give less carbonyl compounds as by-products.

The olefines having 2–4 carbon atoms used in this invention may be in the gaseous or liquid form. Generally, as olefines have small affinity for the reaction liquor (especially in the case of an aqueous solution) and also low solubility towards it, the introduction and mixing of olefines need be carried out with the strongest possible stirring or shaking to quicken the dispersion and diffusion of the olefine into the reaction liquor. When a gaseous olefine is used, the operation can be easily carried out if an excessive olefine is diluted with other gas and circulated forcibly into the reaction liquor.

When the process of this invention is practised, an olefine used as a starting material may be fed to the reaction system at atmospheric pressure, but preferably at an elevated pressure. As the reaction rate is proportional to the concentration of an olefine in the reaction system, and the concentration of olefine, to its partial pressure, the partial pressure of the olefine should preferably be higher than 5 atmospheres, particularly more than 20 atmospheres. In short, any high pressure industrially practicable can be used.

In this invention, it is preferable to react an olefine at a pressure above 5 atmospheres, particularly at least 20 atmospheres. For that purpose, it is preferable that excess olefine be always fed into the reaction system during the progress of the oxidation according to this invention. It is also preferable to feed the olefine all the time during the reaction.

The olefine to be used need not be purified particularly, and an olefine having a purity of more than 90% obtained by the usual petrochemical industry is sufficient. If sulphur or sulphur-containing compound is present in the olefine, it tends to be linked with the thallium to form an insoluble and inert salt. It is desirable therefore to carry out desulfurisation as much as possible.

When an olefine is, according to the conventional method, oxidised with thallic sulphate or thallic nitrate, the yield of alkylene glycol such as ethylene glycol is lowered to a greater degree as the concentration of sulfate ions or nitrate ions in the reaction medium gets greater and the reaction temperature becomes higher (see Controls 6–10 for the influence of the concentration of sulphuric acid ions and Controls 11–22 for the influence by the reaction temperature). According to the conventional method where thallic sulphate or thallic nitrate is used, therefore, it is substantially difficult to increase the concentration of these ions in the reaction medium and to elevate the reaction temperature, and therefore it is difficult to increase the reaction rate.

Therefore, according to the conventional method in which these thallic salts are used, it is impossible under any conditions that the yield of ethylene glycol exceeds 60% of the reacted thallic salt, and moreover a total of about 30–40% of acetaldehyde and higher degree of oxides (Controls 23–32) are always formed. If, however, one follows the procedures of this invention, the yield of alkylene glycol is remarkably increased even if $Cl^-$ and/or $Br^-$ are present in the reaction medium in an atomic ratio of at least 5 against Tl atom, as shown in the attached graph, and moreover, the yield of alkylene glycol is not lowered even if the reaction temperature is elevated. This is one of the merits of the process of this invention.

Hence, the process of this invention can be carried out at 120° to 200°C.

An alkylene halohydrin formed in the reaction system is easily hydrolysed without separation at a temperature of 120° to 200°C. and converted to an alkylene glycol. Therefore, the formed alkylene halohydrin can be hydrolysed in the same reaction system to an alkylene glycol. If the process of this invention is carried out at a temperature of 120°–200°C., the formed alkylene halohydrin is converted continuously into an alkylene glycol in the reaction system, and it is possible to prepare an alkylene glycol at a stretch by the process of this invention.

Since the presence of a free hydrogen halide is detrimental to the hydrolysis of an alkylene halohydrin, it is preferable to minimise the concentration of hydrochloric acid or bromohydroacid. But halogen ions themselves, for instance halogen ions given to the reaction medium by chlorides or bromides, are not detrimental at all.

According to this invention, it has been found that in the said reaction of producing an alkylene glycol, not only by using a thallic salt and chlorine and/or bromine ions in the atomic ratio of these ions/thallium of at least 5, but also by adding to the reaction system a metal salt oxidisable with a molecular oxygen and capable of possessing different valences under the reaction conditions, and furthermore by introducing molecular oxygen into the reaction liquor concurrently with, or separately from the said reaction, it is possible to regenerate a thallous salt [Tl(I)] produced by the formation of the said alkylene glycol to a thallic salt [Tl(III)] and recycle the said thallic salt for use in the said reaction of producing glycol.

As the metal salt oxidisable with oxygen and capable of possessing different valences in the above regeneration reaction, we can cite compounds of a redox metal such as copper, mercury, chromium, manganese, iron, cobalt and nickel. Such metal compounds may be in any form if only they can give ions of their metal in an acid aqueous medium in which chlorine ions and/or bromine ions are present under the conditions specified in the present invention. Preferable compounds are copper bromide, copper chloride, iron bromide, iron chloride, copper oxide, iron oxide, basic copper carbonate, copper sulphate and iron sulphate. As such compounds, all of inorganic acid or organic acid salts of the said metals can be used. Above all, it is convenient to use them in the form of chloride and/or bromide. Furthermore, these metal compounds may be added either in the state of low valence or in the state of high valence.

These metal compounds are used in the form of various salts soluble or insoluble in the medium to be used, but because the reaction is carried out in the copresence of halogen ions, it will be advantageous to use them in the form of halides, especially chlorides or bromides. They are also used in the form of hydroxides or carbonates for the purpose of adjusting the amount of halogen ions used.

The redox metal salts are used ordinally in the amount 1 to 100 times that of the thallic salt in terms of mole ratio, but if necessary, they may be used in a greater amount.

The said regeneration reaction of the thallous salt easily proceeds by mixing and reacting Tl(I) formed by the oxidation of an olefine with a redox-metal salt, halogen ions and molecular oxygen in a neutral or acidic water, an aqueous solution or suspension to produce again Tl(III) according to the following reaction formulas (4) and (5), in which copper is used as the redox metal and chlorine as the halogen.

$$TlCl + 2CuCl_2 \rightarrow TlCl_3 + 2CuCl \qquad (4)$$

$$2CuCl + 2HCl + \tfrac{1}{2}O_2 \rightarrow 2CuCl_2 + H_2O \qquad (5)$$

Both of the reactions (4) and (5) usually proceed concurrently, and Tl(I) is oxidised with the redox metal salt (shown as copper chloride in the formulas) to Tl(III) [refer to formula (4)]. At the same time, the redox metal reduced to a state of low valence is immediately oxidised with molecular oxygen to a high valent state [refer to formula (5)].

But if an iron salt is used as the redox metal salt, only the following reaction corresponding to the formula (4) takes place in the presence of an olefine

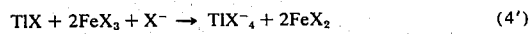

$$TlX + 2FeX_3 + X^- \rightarrow TlX^-_4 + 2FeX_2 \qquad (4')$$

It may be possible to carry out the said reaction separately from the following reaction corresponding to the formula (5)

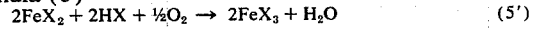

$$2FeX_2 + 2HX + \tfrac{1}{2}O_2 \rightarrow 2FeX_3 + H_2O \qquad (5')$$

The regeneration reaction of thallium proceeds more quickly as the acid concentration is higher, the concentration of halogen ions is higher, the amount of redox metal ions are more than that of thallium ions, and the reaction temperature is higher.

As the molecular oxygen, air can be used, but when oxygen is used, the progress of the reaction becomes more rapid. When they are used under the elevated pressure, it is easier to carry out the reaction. Especially, when the reaction is carried out at a high temperature and elevated pressure, it proceeds sufficiently rapidly in the neutral reaction system without taking trouble of acidifying it.

Thus, the regeneration reaction of thallium proceeds more rapidly as the reaction conditions are severer. But even under mild conditions such as at room temperature, atmospheric pressure and in neutrality, the reaction proceeds and the object of regeneration can be attained. It is therefore possible to bring the conditions of the regeneration conditions into conformity to those of the oxidation reaction of olefines as above mentioned.

Thus, according to the present invention, it is possible to carry out the oxidation of an olefine by which the olefine is oxidised with Tl(III) to glycol, concurrently with, or separately from, the regeneration reaction of thallium salt by which the thus formed Tl(I) is converted into Tl(III) in the presence of a redox metal compound such as Cu(II) and a molecular oxygen. As a result of these reactions, the thallic salt Tl(III) and the redox metal such as Cu(II) can be regarded as merely exhibiting a catalytic action, and alkylene glycol can be continuously produced according to the following formulas

$$CH_2=CH_2 + H_2O + \tfrac{1}{2}O_2 \rightarrow HOCH_2 \cdot CH_2OH \quad (6)$$

As the present invention does not particularly necessitate the isolation and purification of thallium salt and redox metal compounds either in the oxidation reaction of olefines or in the regeneration reaction of thallous salt, an alkylene glycol can be produced from an olefine continuously by very simple operations according to the method of this invention. With respect to the type, concentration, amount and pH of each component in the regeneration reaction of the said thallous salt, however, it is preferable that care should be taken to use the same type, high concentration, great quantity and strong acidity as much as possible within the range not departing from the conditions suitable for oxidation of an olefine and also to adjust the partial pressure of oxygen to a high level.

According to the researches of the inventors, many cationic and anionic ions are not detrimental to the reaction of this invention. For instance, such cations as Li, Na, K, Ca, Be, Mg, Sr, Al, Y, La, Ce, Nd, Yb, Ti, Zr, V, U, Zn, Cd, Ga, In, and Ag are not detrimental and almost inert throughout both the oxidation of olefines and the regeneration reaction of thallium.

The addition of such cations as Pt, Pd, Th and Bi is not detrimental to the regeneration reaction of thallium, but is sometimes not preferable in the oxidation of olefines since they promote the formation of carbonyl compounds or oxidise the formed olefine oxide to a higher degree.

We have stated that any anion of redox metal salt and thallic salt can be used according to this invention, but some of the anions that constitute these metal salts give the following influences and care should, therefore, be taken in this respect.

For instance, such anions as $SO_4$, $ClO_4$, $BF_4$, $PO_4$ and toluenesulfonic acid ions are not harmful to the regeneration reaction of thallium, but these anions tend to form carbonyl compounds or to induce other side-reactions. It is better therefore to avoid the use of too much amount thereof.

$NO_3$ anion promotes the regeneration reaction of thallium, and by the addition of such anion the progress of the reaction becomes remarkably fast. But in the oxidation of olefines, it is dangerous to use $NO_3$ ion in a great quantity as it tends to facilitate the further oxidation.

Sulphur and sulphur compounds are not preferable in both of these reactions. The thallium compounds, redox metal salts and halogens used in the reaction may be of a purity such that can be obtained by the ordinary mining and industrial processes, at which purity the reaction sufficiently proceeds. It is not necessary to purify them particularly.

In the following, various embodiments applicable to the practice of both the oxidation reaction of olefines and the regeneration of thallous salt according to this invention will be explained. Such embodiments are basically as follows:

1. A method by which the whole reactions are carried out in one stage by the use of an olefine and a molecular oxygen.
2. A method by which both of the reactions are carried out in two stages by using an olefine and a molecular oxygen separately.
3. A method by which each of the steps of the said methods (1) and (2) is further divided, if necessary, into many stages.

These embodiments will be explained in detail below.

1. The method by which the whole reactions are carried out in one stage by the use of an olefine and a molecular oxygen can be practised in the following manner.

A reaction vessel is charged concurrently with:
a. water or an aqueous medium,
b. thallic salt [Tl(III)] or thallous salt [Tl(I)],
c. $Cl^-$ and/or $Br^-$ in an amount sufficient to satisfy the specific ratio of $Cl^-$ and/or $Br^-$ to Tl mentioned above, and,
d. the said compound of the redox metal (the valence of the metal may be high or low), and then an olefine and a molecular oxygen are fed into the vessel at the same time.

By these procedures, it is possible to carry out (A) the oxidation reaction of an olefine and (B) the regeneration reaction of a thallous salt to convert it to a thallic salt, concurrently in one vessel.

The reason why in this embodiment a thallous salt or a salt of a high valence or low valence redox metal can be charged into the vessel is that the feeding of a molecular oxygen into the reaction vessel leads to the conversion of the thallous salt into a thallic salt to carry out the oxidation reaction, and in the meantime, the salt of a low valence redox metal is also converted into that of a high valence redox metal as mentioned above.

This method needs only simple operations, and is suitable for continuous operation. When an alkylene glycol is to be produced by using this method, the amount of hydrochloric acid or hydrobromic acid generated by the oxidation reaction may be substantially equal to that of the hydrochloric acid or hydrobromic acid consumed in the regeneration reaction as shown by the said formula (5) to maintain the acidity of the reaction liquor almost constant during the reaction, and the control of the reaction is not complicated.

When this method is practised, an olefine and a molecular oxygen concurrently exist in the reaction system and there may be a danger of explosion. Also disadvantageously, a pure oxygen should be used because the use of an inexpensive air causes the accumulation of nitrogen in the circulating gas with the progress of reaction and leads to the decrease in the reaction ratio per volume of the apparatus used.

2. The method by which both of the reactions are carried out in two stages by using an olefine and a molecular oxygen separately can be effected in the following manner.

In this case, an olefine-fed zone is separated from a zone into which the feed a molecular oxygen. In the olefine-feeding zone, the oxidation reaction is carried out in the presence of a thallic salt in accordance with the conditions of the present invention, whereby an alkylene glycol is produced as mentioned above. Into the second zone, oxygen is fed and the regeneration of the thallous salt is effected.

This method may be carried out by the use of one reactor having two reaction zones, one reactor for each of these zones or one reactor where these reactions are to be alternately carried out. In the following, we shall direct our explanation to the case where the method is carried out by using one reactor for each of the reactions.

When an alkylene halohydrin is formed in a first reactor for oxidation, the reaction liquor is introduced into a second reactor for regeneration reaction where the thallous salt is regenerated with a molecular oxygen and at the same time, the said alkylene halohydrin can be hydrolysed to an alkylene glycol. This is because the afore-mentioned conditions for the regeneration reaction of thallous salt can be directly applied as the conditions for the hydrolysis of an alkylene halohydrin.

If the reaction conditions in the said first reactor for oxidation are appropriately adjusted so as to make it possible to hydrolyse the formed halohydrin concurrently with or subsequently to its formation, an alkylene glycol can be prepared mainly in situ in the first reactor for oxidation. Incidentally, as the rate of the hydrolysis reaction of an alkylene halohydrin is generally slower than that of the reaction to form an alkylene halohydrin by oxidation of an olefine, it is more advantageous to continuously transfer the reaction liquor in the first oxidation reactor to the second regeneration reactor where an alkylene glycol is formed concurrently with the regeneration than to make it stay for a long time in the first reactor and form an alkylene glycol there.

The redox metal compound may be put into the said second reactor or into the first reactor in advance. In general, the redox metal compound does not impede the oxidation reaction in the first reactor. When a high valence iron (for instance, trivalent) iron compound is used as the redox metal compound in the first reactor, the thallous salt formed here is converted into a thallic salt in an amount corresponding to the said iron compound without supplying a molecular oxygen particularly into the first reactor [refer to formula (4')], and offered for the oxidation reaction.

The afore-mentioned method can be practised either batchwise or continuously. As an olefine and oxygen are each fed into different reactor according to this method, there is utterly no danger of explosion and air can be advantageously used as the oxygen source. But the operation of the reaction becomes complicated as compared with the said one-stage method because of dividing one reactor into two. The control of the reactions also becomes complicated.

As mentioned above, the oxidation reaction of an olefine is a reaction to produce hydrochloric acid or hydrobromic acid, and the regeneration reaction is one to consume these acids. In the said one-stage method, the amount of them are both equal and the control of the reaction is easy. According to the present method, the acid concentration tends to increase in the oxidation reactor, but to decrease in the regeneration reactor. Since a remarkable fluctuation of the acid concentration in each of these reactions is not preferable, it becomes necessary to adjust the amount of olefines or oxygen to be fed or the reaction temperature, or to add or withdraw the acid.

3. In the said methods (1) and (2), it is not necessary to carry out each of the reactions in one stage, and various modifications can be used.

For example, the oxidation reaction and the regeneration reaction can be carried out in one or more reactors concurrently or separately by dividing a reaction zone for each reaction into a low temperature reaction zone and a high temperature reaction zone or into more than two zones. In this case, the reaction zones for both the oxidation and regeneration reactions may be optionally combined with each other. By optionally combining such procedures, the reactions can be easily controlled, explosion can be prevented, and a continuous operation can be smoothly carried out.

Procedures of separating the reaction products obtained according to the method of this invention will now be detailed.

The reaction products can be recovered by withdrawing part or whole of the reaction liquor after the completion of each reaction or after passing through a reaction zone or at an optional stage during the reaction.

1. Separation of Alkylene Glycol

The alkylene glycol can be easily separated from the reaction liquor by the method known per se such as extraction, distillation, concentration and ion exclusion, and can be purified by the known purifying means.

2. Other matters

The formation of a small amount of aldehydes or ketones is inevitable even by the method of this invention. Since these compounds are by themselves useful and they cause the consumption of a thallic compound or induce the formation of high molecular weight impurities, it is preferable to separate them immediately.

As these compounds are relatively low boiling substances, they can be separated and recovered by the same procedures as used in the separation of halohydrin singly or before or after the separation of halohydrin when the separation of halohydrin is effected.

The apparatus to be used in this invention is not particularly restricted, but consideration as to the corrosion is necessary with respect to the portion which contacts halogen, particularly oxygen and halogen in acidic condition. Usually, preferable apparatus are those lined with titanium, titanium alloy, tantalum, glass, enamel, and thermoplastic or thermosetting resins such as fluorine resin.

The thallium or redox metal salts used in this invention may be used in the form of suspension. Tl(I) produced by the oxidation of an olefine is liable to be precipitated in liquor in the presence of halogen ions in the form of thallic halide (or complex salts of thallous halide and thallic halide $TlCl_3·3TlCl$) which has low solubility in water or many of the used aqueous media, and the redox metal salts also take the form of cuprous chloride or iron hydroxide which is insoluble in aqueous media. An appropriate care should therefore be necessary in respect of the reaction and transportation of such a suspension. Consideration is also necessary to ensure a sufficient dispersion of such a gas as an olefine and oxygen into the liquor. A small amount of a surface active substance may be added in order to make the contact of gas-liquid, solid-liquid and gas-liquid-solid sufficient.

The regeneration of the thallous salt formed when an alkylene glycol is prepared by oxidising the said olefine according to the method of this invention need not always be carried out in the form such that it is contained in the reaction liquor just after the oxidation reaction. According to another procedure, a thallium salt predominantly comprising a thallous salt is separated from the said reaction liquor by the known separating means such as filtration and centrifugal separation, and then it can be regenerated to a thallic salt by contact with a molecular oxygen in the presence of a compound of a redox metal in an acidic or neutral aqueous medium. The thallic salt so regenerated can of course be used in the oxidation reaction of this invention. When the redox metal compound is optionally separated from the thallic salt in the said regeneration, there can be employed a method by which the redox metal compound is first precipitated and separated by concentrating it or a method by which it is separated by the use of an ion-exchange resin. But preferably, they should be separated from each other by solvent-extraction using oxygen-containing organic solvents such as ether, ester and ketone, particularly ethyl ether, isopropyl ether, methyl isobutyl ketone and diisobutyl ketone.

In the above-mentioned extraction, the thallic compound is extracted with such solvents from an aqueous solution of hydrohalogenic acid in the form of halogenothallic acid ($HTlX_4$, X being halogen). On the other hand, hydrohalogenic acid, copper chloride and thallous compound are not at all extracted. When iron salt is used in the regeneration step, it is preferable to adjust the acid concentration of the aqueous solution to about 2 N, and to carry out the extraction with the use of an ether type solvent, and it is preferable to employ lower extraction temperatures. The thallic compound extracted may be recovered by evaporating the organic solvent under reduced pressure or may be recovered by re-extraction with a warm water utilising the difference of the distributing coefficient.

This invention will be explained hereinafter by Examples and Controls in which the parts are by weight and the identification and quantitative determination of the product were performed by the following methods.

| Tl(III): | Oxidation-reduction titration (Iodometry) Weight analysis (neutralisation method) |
|---|---|
| Ethylene glycol: | Gas chromatography Oxidation-reduction titration (per-iodic acid oxidation method) |
| Acetaldehyde: | Poralography Weight-analysis (2,4-dinitrophenylhydrazine method; all carbonyl compounds are calculated as acetaldehyde |
| Ethylene halohydrin: | Gas chromatography Volume analysis (halogen titration method) |
| Others: | Gas chromatography Infrared spectrophotometry others |

EXAMPLES 1 – 5 AND CONTROLS 1 – 3

An aqueous solution containing 0.2 mole/liter of thallic chloride ($TlCl_3$) and various concentrations of sodium chloride or hydrogen chloride was reacted in a pressurised reactor by introducing excess ethylene (the pressure of ethylene being 50 kg/cm² gauge) while stirring and heating it from outside.

The products obtained after 4 hours' reaction and their yields are shown in Table 1.

Table 1

Cl⁻/Tl(III) Atomic Ratio and Yield of Products

| | Cl⁻/Tl(III) atomic ratio (Concentration at the initiation of reaction) | Yield of products [mol % based on the consumed Tl(III)] | | |
|---|---|---|---|---|
| | | EG | ECH | AA |
| Control 1 | 2.0<sup>a)</sup> | 40 | 1 | 19 |
| 2 | 3.0 | 52 | 2 | 21 |
| 3 | 4.0<sup>b)</sup> | 62 | 4 | 21 |
| Example 1 | 5.0<sup>c)</sup> | 70 | 3 | 19 |
| 2 | 7.0<sup>c)</sup> | 74 | 4 | 14 |
| 3 | 10.0<sup>c)</sup> | 77 | 6 | 13 |
| 4 | 15.0<sup>c)</sup> | 80 | 4 | 12 |
| 5 | 20.0<sup>c)</sup> | 81 | 4 | 12 |

<sup>a)</sup>Thallic hydroxide (Tl(OH)₃) and HCl were employed instead of TlCl₃.
<sup>b)</sup>TlCl₃ + HCl
<sup>c)</sup>TlCl₃ + NaCl

EXAMPLES 6 – 8

Thallic hydroxide [Tl(OH)₃] (2.93 parts) was dissolved into 60 parts of an aqueous hydrochloric acid, and the solution was heated to 140°C. in a pressurised reactor. While stirring the vessel vigorously, ethylene was introduced (the pressure of ethylene being 50–52 kg/cm² gauge). The products obtained after 4 hours' reaction and their yields are shown in Table 2.

Table 2

| | Concentration of hydrochloric acid (N; initial concentration) | Yield of Products (mole % based on the thallium) | | | |
|---|---|---|---|---|---|
| Examples | | Ratio of Tl(III) reacted | Ethylene glycol | Acetaldehyde | Ethylene chlorohydrin |
| 6 | 1.0 | 100 | 69.8 | 17.3 | 5.0 |
| 7 | 2.0 | 100 | 69.9 | 12.5 | 9.0 |
| 8 | 3.0 | 100 | 60.3 | 10.3 | 18.6 |

EXAMPLES 9 – 10

Thallic hydroxide [Tl(OH)₃] (2.93 parts and sodium chloride were dissolved into 60 parts of 0.6 N aqueous hydrochloric acid, and the solution was heated to 140°C. in a pressurised reactor. While stirring the vessel vigorously, ethylene was introduced (the pressure of ethylene being 50–52 kg/cm²). The products obtained after 4 hours' reaction and their yields are shown in Table 3.

Table 3

Amount of Sodium Chloride Added and Yield of EG

| | | Yield of Products (mole % based on the thallium) | | | |
|---|---|---|---|---|---|
| Examples | Amount of sodium chloride added (parts) | Ratio of Tl(III) reacted | Ethylene glycol | Acetaldehyde | Ethylene chlorohydrin |
| 9 | 4.90 | 100 | 77.2 | 13.6 | 4.2 |

Table 3-continued

Amount of Sodium Chloride Added and Yield of EG

Yield of Products (mole % based on the thallium)

| Examples | Amount of sodium chloride added (parts) | Ratio of Tl(III) reacted | Ethylene glycol | Acetaldehyde | Ethylene chlorohydrin |
|---|---|---|---|---|---|
| 10 | 8.40 | 100 | 80.0 | 12.4 | 3.6 |

EXAMPLE 11

Thallic hydroxide [Tl(OH)$_3$] (2.93 parts) and 8.4 parts of sodium chloride were dissolved in an aqueous solution of tetramethylene glycol in 0.6 N hydrochloric acid (16% by volume). The solution was put into a pressurised reactor, and ethylene was introduced to a pressure of 45 kg/cm$^2$ gauge. While stirring the vessel vigorously, the reaction mixture was heated and reaction was carried out at 140°C.

Analysis of the product at the end of 4 hours period indicated that there was no Tl(III) and ethylene glycol, acetaldehyde and ethylene chlorohydrin were obtained at the yield of 60.2 mole %, 6.8 mole % and 8.6 mole %, respectively, based on the added thallium.

EXAMPLE 12

Thallic bromide (TlBr$_3$) was dissolved in an aqueous solution of sodium bromide (NaBr) to adjust the Tl(III) concentration to 0.2 mole/liter and the Br$^-$ concentration to 1.2 mole/liter. Ethylene was introduced into a pressurised reactor (the pressure of ethylene being 50 kg/cm$^2$). While stirring vigorously, the vessel was heated from outside and reaction was carried out at 120°C. for 3 hours. The reaction product and their yield are as follows:

| | |
|---|---|
| Ratio of Tl(III) reacted | 100% |
| Yield of Product (mole % based on the reacted thallium) | |
| Ethylene glycol | 73 |
| Acetaldehyde | 7 |
| Ethylene bromohydrin | 6 |

EXAMPLES 13 – 18 AND CONTROLS 4 – 5

An aqueous solution containing 0.2 mol/liter of thallic chloride and 1.4 mol/liter of sodium chloride with a Cl$^-$/Tl(III) atomic ratio of 10 was reacted in a pressurised reactor by introducing ethylene while vigorously stirring and heating it from outside (the pressure of ethylene being 60 kg/cm$^2$).

The products obtained after 3 hours' reaction and their yields are shown in Table 4.

Table 4

Reaction Temperature and Yield of EG

Yield of Products (mole % based on the reacted thallium)

| | Reaction temperature (°C.) | Ratio of Tl(III) reacted | Ethylene glycol | Acetaldehyde | Ethylene chlorohydrin |
|---|---|---|---|---|---|
| Example 13 | 200 (reaction) | 100 | 55 | 28 | — |
| 14 | 170 | 100 | 65 | 21 | 3 |
| 15 | 160 | 100 | 72 | 19 | 3 |
| 16 | 150 | 100 | 78 | 17 | 5 |
| 17 | 130 | 100 | 55 | 12 | 29 |
| 18 | 120 (reaction time being 5 hours) | 100 | 47 | 10 | 41 |
| Control 4 | 100 (reaction time being 5 hours) | 100 | 10 | 8 | 80 |
| 5 | 70 (reaction time being 8 hours) | 98 | 8 | 8 | 82 |

EXAMPLES 19 – 23

Thallic hydroxide [Tl(OH)$_3$] (2.55 parts) was dissolved in 100 parts of 1.2 N aqueous hydrochloric acid, and reacted in a pressurised reactor by heating to 160°C. while introducing ethylene under stirring. The products after 1 hour reaction and their yields are shown in Table 5.

Table 5

Reaction Pressure and Yield of EG

Yields of Products (mole % based on the consumed thallium (III)

| Examples | Reaction pressure (kg/cm$^2$ gauge) | Ratio of Tl(III) reacted | Ethylene glycol | Acetaldehyde | Ethylene chlorohydrin |
|---|---|---|---|---|---|
| 19 | 8 | 95 | 78 | 17 | 3 |
| 20 | 28–30 | 100 | 77 | 16 | 1 |
| 21 | 42–46 | 100 | 76 | 18 | 0 |
| 22 | 75–78 | 100 | 77 | 17 | 2 |
| 23 | 78–79 (ethylene/ethane (1:1)) | 100 | 75 | 15 | 2 |

As seen from Table 5, the yield of ethylene glycol is not changed by the pressure of ethylene, but the speed of formation of ECH gets faster in proportion to the pressure of ethylene. In other words, it is understood from this, the formation of ECH by the oxidation of ethylene and the formation of EG by the hydrolysis of ECH are two independent reactions.

EXAMPLES 24 – 27

Thallic chloride (TlCl$_3$.2H$_2$O) (69.2 parts) was dissolved into 1000 parts of 0.5 N aqueous hydrochloric acid, and while stirring the solution vigorously in a pressurised reaction vessel, various olefines were added and the reaction was carried out at a temperature of 140°–170°C. (the pressure of olefine being 20–43 kg/cm$^2$ gauge). The products obtained after 2 hours' reaction and their yields are shown in Table 6.

Table 6

Preparation of Glycol from Various Olefines
Yield of Products
(mole % based on the thallium)

| Examples | Olefine | Ratio of Tl(III) reacted | Glycol | Carbonyl compounds |
|---|---|---|---|---|
| 24 | Ethylene | 100 | Ethylene glycol 76 | Acetaldehyde 17 |
| 25 | Propylene | 100 | Propylene glycol-1,2 50 | Acetone 29 |
| 26 | Butene-1 | 100 | Butylene glycol-1,2 51 | Methyl ethyl ketone 14 |
| 27 | Isobutene | 100 | 2-methylpropylene glycol-1,2 30 | Isobutylaldehyde 11 |

EXAMPLE 28

Thallic hydroxide [Tl(OH)$_3$] (25.5 parts) and 42.6 parts of cupric chloride (CuCl$_2$.2H$_2$O) were dissolved into 1000 parts of a 0.60 N aqueous hydrochloric acid, and heated to 160°C. in a pressurised reactor. Ethylene was introduced thereinto (pressure being 72–74 kg/cm$^2$ gauge) and reaction was carried out for 2 hours while vigorously stirring.

After 2 hours from the start of the reaction, a part of the product was identified and quantitatively determined, and it was found that thallium (III) was consumed 100% and converted into thallium (I), and that ethylene glycol and acetaldehyde were formed at the yield of 89 mole % and 6 mole % against the thallium (III).

The unreacted ethylene was expelled from the reactor, and oxygen (pressure being 6–7 kg/cm$^2$ gauge) was introduced thereinto. Heating was done to 150°C. for 1 hour while stirring to thereby regenerate the thallium.

Likewise, ethylene was again introduced into the reactants and oxidised. Then, the thallium was again regenerated. Thus, the cycle of the oxidation of ethylene and the regeneration of thallium was repeated 10 times to carry out the reaction under the same conditions as mentioned above.

As a result, 43.6 parts of ethylene glycol, 22 parts of acetaldehyde, 0.9 part of ethylene chlorohydrin, and a small amount of condensate and the chloride of ethylene (mixture) were obtained.

EXAMPLE 28

Thallous chloride (TlCl) (2.4 parts), 77.8 parts of ferric chloride (FeCl$_3$.6H$_2$O) were dissolved into 50 parts of 1N aqueous hydrochloric acid (part of TlCl being suspended) to adjust the amount of the entire solution to 300 parts. The solution was then heated to 160°C. in a pressurised reactor. First, air was introduced for 20 minutes at a pressure of 20 kg/cm$^2$ gauge, and the reactants were vigorously stirred. (In 20 minutes after introduction of air, more than 80% of TlCl was converted into TlCl$_3$.) Then, air was expelled from the reactor, and ethylene was introduced for 20 minutes at a pressure of 20 kg/cm$^2$ gauge.

Again, air was introduced in the same manner as above mentioned, and alternately ethylene was further flowed. This cycle was repeated 5 times (the introduction of air being 5 times for a total period of 100 minutes and the introduction of ethylene being 5 times for a total period of 100 minutes), and thus, the oxidation of ethylene and the regeneration of thallium were carried out alternately. All this while, the heating and stirring operations were continued. Therefore, the hydrolysis of the formed chlorohydrin was continuously carried out.

Acetaldehyde formed during the reaction (and a small amount of chloroacetaldehyde and crotonealdehyde) came out of the reactor together with the flowing gas, and so was collected in a cold water.

Consequently, 5.0 parts of ethylene glycol, 0.5 part of acetaldehyde and 1.2 parts of ethylene chlorohydrin were obtained.

In this Example, the amount of glycol and chlorohydrin formed is stoichiometrically greater than the total amount of Tl(III) repeatedly regenerated by air ([5 times the initial amount of Tl(I)]. It is understood therefore that during the flowing of ethylene oxidation reaction is repeatedly carried out while the Tl(I) is regenerated by Fe(III).

EXAMPLE 29

Thallic hydroxide [Tl(OH)$_3$] (7.7 parts) and 51.0 parts of cupric chloride (CuCl$_2$.2H$_2$O) were dissolved into water to make 300 parts of a solution. The solution was heated to 150°C. in a pressurised reactor, and contacted with ethylene flowed for 20 minutes at a pressure of 20 kg/cm$^2$ gauge. Then, air was flowed into this reaction liquor for 20 minutes at a pressure of 20 kg/cm$^2$ gauge.

The cycle of contacting the reaction liquor with ethylene and air was alternately repeated five times (the contacting with ethylene five times for a total period of 100 minutes; the contacting with air five times for a total period of 100 minutes), the reaction was carried out.

Consequently, 7.5 parts of ethylene glycol, 0.3 part of acetaldehyde and a small amount of ethylene chlorohydrin were formed.

When the same reaction was carried out by the use of 67.2 parts of cupric bromide (CuBr$_2$) instead of the cupric chloride at 130°C. with a total of 10 cycles, 16.1 parts of ethylene glycol, 0.2 part of acetaldehyde and a small amount of ethylene bromohydrin were formed.

Again, when the same reaction was carried out by the use of 25.5 parts of cupric bromide instead of the cupric chloride at 130°C. with a total of 10 cycles, 16.7 parts of ethylene glycol and 0.3 part of acetaldehyde were formed.

EXAMPLE 30

Thallous chloride (TlCl) (24.0 parts) and 170.4 parts of cupric chloride (CuCl$_2$.2H$_2$O) were dissolved into 1000 parts of 1.0 N aqueous hydrochloric acid (a part of TlCl being suspended), and the solution was heated to 140° – 170°C. in a circulating pressurised reactor. Reaction was carried out while a gaseous mixture of ethylene with oxygen (9.2% by volume of ethylene and 8% by volume of oxygen) was introduced at a pressure of 20 kg/cm² gauge.

The oxidation of ethylene and the regeneration of thallium took place simultaneously, and ethylene glycol and acetaldehyde were obtained at the yield of 8.7 and 6 mole % respectively based on the consumed ethylene.

When this reaction was carried out in an aqueous solution of 1.0 N hydrochloric acid and ethylene glycol (the volumetric ratio of ethylene glycol to water being 1:10) instead of 1.0 N aqueous hydrochloric acid, the lowering of the yield of the product was very slight.

However, when this reaction was carried out in 1.0 N hydrochloric acid/ethylene chlorohydrin aqueous solution (the weight ratio of ethylene chlorohydrin to water being 8:93), the yield of ethylene (after substraction of the yield of ethylene glycol formed by hydrolysis of chlorohydrin present in the solvent in advance) was somewhat increased.

EXAMPLE 31

Thallous chloride (TlCl) (72 parts), 135 parts of ferric chloride (FeCl$_3$·6H$_2$O), 17 parts of cupric chloride (CuCl$_2$·2H$_2$O) 500 parts of 1 N aqueous hydrochloric acid were dissolved into water to make 1000 parts of a solution (a part of TlCl being suspended), and the solution was heated to 160°C. in a gas-circulating type pressurised reactor. Reaction was carried out for 3 hours while a gaseous mixture of ethylene and oxygen (96% by volume of ethylene and 4% by volume of oxygen) was introduced at a pressure of 35 kg/cm² gauge.

Acetaldehyde formed during the reaction came out of the reaction system together with the flowing gas, and was collected in a cold water.

As a result of the reaction, 102 parts of ethylene glycol, 11 parts of acetaldehyde and 32 parts of ethylene chlorohydrin were obtained.

EXAMPLES 32 – 34

Thallic chloride (TlCl$_3$·2H$_2$O) (69.2 parts), 170.4 parts of cupric chloride (CuCl$_2$·2H$_2$O) and 74.6 parts of potassium chloride (KCl) were dissolved into water to make 1000 parts of a solution. The solution was heated in the same manner as in Example 30 in a pressurised reactor to 140°–170°C. by adding oxygen and various olefines concurrently. The results are shown in Table 7.

Table 7

| | | Preparation of glycols from various olefines Yield of products (mole % based on the reacted olefine) | | | |
|---|---|---|---|---|---|
| Examples | Olefines | Glycols | | Carbonyl compounds | |
| 32 | Ethylene | Ethylene glycol | 85 | | 6 |
| 33 | Propylene | Propylene glycol | 62 | Acetone | 31 |
| 34 | Butene-1 | Butylene glycol | 47 | Methyl ethyl ketone | 20 |

EXAMPLE 35

A pressure reactor equipped with a stirrer was charged with 60 parts of 0.8 N aqueous hydrochloric acid and 2.98 parts of thallic hydroxide. The solution was heated to 140°C. and while vigorously stirring, ethylene was introduced to a pressure of 50 atmospheres. Thus, the reaction was carried out for 4 hours.

The analysis of the reaction product indicated that there was no thallic salt therein and 61.5 mole % of ethylene glycol, 4.0 mol % of ethylene chlorohydrin and 20.8 mole % of acetaldehyde, based on the amount of the thallium used, were obtained. The precipitate was filtered and 2.43 parts of thallous chloride was obtained. To the thallous chloride were added 100 parts of 3 N aqueous hydrochloric acid and 10 parts of cupric chloride. The mixture was heated and stirred for 6 hours, and oxygen was introduced. After cooling, the mixture was extracted with 150 parts of ethyl ether. The ethyl ether was removed by distillation under reduced pressure, and by dilution with water, 60 parts of an aqueous hydrochloric acid solution of thallium chloride free from copper ions was obtained. The thallic chloride contained therein is 99.5% of the thallic salt used initially, and the composition of the solution (ratio of hydrochloric acid to thallium) is almost the same as that of the initial solution. When ethylene was oxidised by the use of this solution, the results were the same as those obtained by the above-mentioned solution.

The Control Examples shown below indicate the results of oxidation reaction of an olefine with a thallium salt carried out under various conditions.

CONTROLS 6 – 10

Thallic hydroxide Tl(OH)$_3$ was dissolved and partly suspended into an aqueous sulphuric acid solution of various concentrations, and while stirring vigorously, ethylene was introduced at 20°C. After the end of the absorption of ethylene into the solution, stirring was rather continued for 30 to 40 minutes, when the reaction was terminated and the analysis of the product was conducted. The results are shown in Table 8.

Table 8

Oxidation of ethylene with thallic salt in sulphuric acid
Acid concentration and yield (atmospheric pressure, 20°C.)

| Controls | Concentration of sulphuric acid at the initiation of reaction (N) | Concentration of Tl(III) at the initiation of reaction (mole/liter) | Yield of Product based on the consumed Tl(III) | | Calculated on the basis of the amount of ethylene absorbed (mole %) |
|---|---|---|---|---|---|
| | | | EG | AA (acetaldehyde and glycol aldehyde calculated as acetaldehyde) | |
| 6 | 0.5 | 0.05 | 48 | 30 | 85 |
| 7 | 25 | | 40 | 36 | 73 |
| 8 | 4.0 | | 34 | 36 | 67 |
| 9 | 6.2 | | 30 | 38 | 67 |
| 10 | 125 | | 16 | 30 | 48 |

CONTROLS 11 – 22

The oxidation of ethylene was carried out under the same conditions as in Controls 6–10 at various temperatures. The results are shown in Table 9.

Table 9

| Control | Acid | Concentration of acid at the initiation of reaction (N) | Concentration of Tl(III) at the initiation of reaction (mole/liter) | Reaction temperature (°C.) | Yield of Product based on the consumed Tl(III) | | Ratio of reaction (mole %) (Calculated from amount of absorbed ethylene) |
|---|---|---|---|---|---|---|---|
| | | | | | EG | AA (acetaldehyde and glycol aldehyde calculated as acetaldehyde) | |
| 11 | H₂SO₄ | 0.50 | | 0 | 53 | 18 | 82 |
| 12 | | | | 20 | 48 | 30 | 85 |
| 13 | | | | 50 | 44 | 41 | 89 |
| 14 | | | | 70 | 40 | 37 | 79 |
| 15 | | | | 90 | 28 | 20 | 52 |
| 16 | HBF₄ | 0.92 | | 20 | 60 | 37 | 100 |
| 17 | | | | 40 | 58 | 40 | 98 |
| 18 | | | | 50 | 56 | 38 | 95 |
| 19 | | | | 70 | 47 | 26 | 71 |
| 20 | | | | 90 | 28 | 11 | 40 |
| 21 | HNO₃ | 1.00 | | 30 | 32 | 29 | — |
| 22 | | | | 50 | 22 | 31 | — |

CONTROLS 23 – 32

The oxidation of ethylene was conducted under the same conditions and procedures as in Controls 6–10 in an aqueous solution of various acids. The results are shown in Table 10.

Table 10

Oxidation of ethylene with thallic salt of various acids
(atmospheric pressure, 20°C.)

| Controls | Acid | Concentration of acid at the initiation of reaction (N) | Concentration of Tl(III) (mole/liter) | Reaction time (hour) | Yield of Product (mole % based on the consumed Tl(III)) | | Ratio of reaction calculated from the amount of ethylene absorbed or consumed Tl(III) (mole %) |
|---|---|---|---|---|---|---|---|
| | | | | | EG | AA (acetaldehyde and glycol aldehyde as acetaldehyde) | |
| 23 | H₂SO₄ | 0.72 | 0.07 | 2 | 50.0 | 33.8 | 101 |
| 24 | HNO₃ | 0.2 | 0.03 | " | 45.4 | 43.0 | 92.8 |
| 25 | HClO₄ | 2.70 | 0.90 | " | 30.9 | 62.9 | — |
| 26 | HBF₄* | 2.46 | 0.10 | 7 | 55.0 | 43.3 | 103 |
| 27 | HOAC | 1.72 | 0.10 | (30°C)3.5 | 50 | 23 | 20 |
| 28 | H₃PO₄ | 4.0 | 0.10 | (30°C)6 | 29 | 35 | 96.1 |
| 29 | HCl | 0.40 | 0.09 | 42 | 1 | 0 | 8 |
| 30 | " | " | " | (40°C)28 | 9 | 0 | 17 |
| 31 | " | " | " | (70°C)14 | 14 | 1 | Ca 38 |
| 32 | H₂SO₄ } HCl | 0.60 } 0.40 | 0.10 | 30 | 1 | 2 | Ca 9 |

Controls 33–46 show the results of extraction of Tl(III) with various organic solvents and the re-extraction of Tl(III) with water from the extract.

CONTROLS 33 – 42

An aqueous hydrochloric solution of thallic chloride of various compositions was extracted with the same amount of an organic solvent, and the thallic chloride was almost completely extracted in the form of HTlCl$_4$. The cupric ions were not extracted under the same conditions. The results are shown in Table 11.

Table 11

| | Extraction of Tl(III) by organic solvent | | | | |
|---|---|---|---|---|---|
| Control | Organic solvent | Temperature | Composition of aqueous solution (mole concentration) | | Ratio of extraction | Composition of extract (Cl/Tl mole ratio) |
| | | | Tl$^{+3}$ | Cl$^-$ | (mole %) | |
| 33 | Ethyl ether | 20 | 0.190 | 4.61 | 99.8 | 41.8 |
| 34 | Ethyl ether | '' | '' | 6.18 | '' | 4.54 |
| 35 | Ethyl ether | '' | 0.500 | 4.47 | 99.2 | 4.18 |
| 36 | Methylisobutyl ketone | '' | 0.190 | 1.45 | 99.6 | 5.95 |
| 37 | | '' | '' | 4.61 | 99.7 | 3.70 |
| 38 | Isopropyl ether | 24.7 | 0.284 | 3.95 | 98.2 | 3.94 |
| 39 | Diisobutyl ketone | 24.0 | 0.190 | 4.73 | 97.2 | 3.93 |
| 40 | | '' | 0.284 | 3.95 | 92.3 | 3.95 |
| 41 | Ethyl ether* | 20.0 | 0.190 | 5.42 | 99.8 | |
| 42 | Ethyl ether* | '' | 0.190 1.600 | 6.62 | ≅0.0** 99.8 0.2** | |

Note:
*Example in which thallium (III) and copper (II) are jointly present.
**Values with respect to cupric ions coordinated.

When in the procedures of Controls 33–42 an organic solvent solution of the HTlCl$_4$ was contacted with a warm water, a hydrochloric acid aqueous solution of thallic chloride was obtained. The results are shown in Table 12.

Table 12

| | Re-extraction of Tl(III) by water | | | | |
|---|---|---|---|---|---|
| Controls | Organic solvent | Temperature (°C.) | Composition of organic solvent (mole concentration) | | Ratio of extraction of Tl | Composition of extract (Cl/Tl mole ratio) |
| | | | Tl$^{+3}$ | Cl$^-$ | (mole %) | |
| 43 | Isopropyl ether | 30 | 0.212 | 0.917 | 41.2 | 4.09 |
| 44 | Isopropyl ether | 50 | 0.212 | 0.974 | 50.7 | 4.07 |
| 45 | Diisobutyl ketone | 30 | 0.203 | 1.04 | 75.2 | 4.07 |
| 46 | Diisobutyl ketone | 40 | 0.203 | 1.04 | 83.9 | 4.12 |

CONTROL 47

200 ml. of a 0.41 mole/liter solution of thallic chloride in 0.10 mole/liter of aqueous hydrochloric acid were placed in a glass reaction vessel provided with a stirrer and gas inlet and outlet tubes. The pH of the solution was adjusted to 2.1 by addition of sodium hydroxide. The solution was maintained at 20°C., and ethylene gas was circulated therein to react it. The ethylene gas circulated in a closed circuit provided with a gas burette. An amount of the gas absorbed during the reaction was measured, and the pressure within the circuit was always maintained at one atmosphere.

During the reaction, a part of the solution was taken out from time to time, and the produced ethylene glycol (EG for short), ethylene chlorohydrin (ECH for short), acetaldehyde (AA for short) and the consumed Tl were quantitatively analyzed.

Absorption of ethylene was so slow that even after a lapse of 48 hours, only less than 20 % of ethylene was reacted based on Tl(III). The analysis of the products after a lapse of 8-hour reaction showed the following results.

| | |
|---|---|
| Amount of ethylene absorbed: | 0.033 mol/liter [8 % based on initial Tl(III)] |
| Amount of Tl(III) reacted: | 0.029 mole/liter [7 % based on initial Tl(III)] |
| EG: | 0.006 mole/liter [about 20 % yield based on the reacted Tl(III)] |
| AA: | 0.003 mole/liter [about 10 % yield based on the Tl(III) reacted] |
| ECH: | 0 |

This means that the reaction did not virtually proceed.

What is claimed is:

1. A process for the preparation of an alkylene glycol having 2 to 4 carbon atoms, which comprises contacting an unsubstituted aliphatic olefin having 2 to 4 carbon atoms with an aqueous solution containing chlorine ions, bromine ions or a mixture thereof and thallic ions (TlIII) at a temperature of 120°C. to 200°C. and a partial pressure of said olefin of above 5 atmospheres, the atomic ratio of said chlorine ions, bromine ions or mixture thereof to said thallic ions being at least 6.

2. The process of claim 1 wherein $TlCl_3$ or $TlBr_3$ produces said thallic ions.

3. The process of claim 1 wherein a metal salt capable of possessing a different valence under the reaction conditions and oxidizable with oxygen selected from $CuCl_2$, $CuBr_2$, $FeCl_3$ and $FeBr_3$ is added to the reaction system, and oxygen is introduced into the reaction system in the presence or absence of an olefin.

4. The process of claim 1 wherein said unsaturated olefine is selected from the group consisting of ethylene and propylene.

* * * * *

UNITED STATES PATENT AND TRADEMARK OFFICE
CERTIFICATE OF CORRECTION

PATENT NO. : 3,950,440
DATED : April 13, 1976
INVENTOR(S) : Isao Hirose et al

It is certified that error appears in the above-identified patent and that said Letters Patent are hereby corrected as shown below:

Item 30, please change the Foreign Application Priority Data so as to include the following:

-- March 11, 1966   Japan ............................ 41-15045
   Oct. 19, 1966    Japan ............................ 41-68820
   Dec. 13, 1966    Japan ............................ 41-81633 --

Signed and Sealed this

Third Day of August 1976

[SEAL]

Attest:

RUTH C. MASON
Attesting Officer

C. MARSHALL DANN
Commissioner of Patents and Trademarks